United States Patent
Chang et al.

(10) Patent No.: US 11,833,176 B2
(45) Date of Patent: Dec. 5, 2023

(54) COMPOSITION FOR TREATING NEONATAL HIE

(71) Applicant: MEDINNO INC., Gyeonggido-do (KR)

(72) Inventors: Yun Sil Chang, Seoul (KR); Won Soon Park, Seoul (KR); So Yoon Ahn, Seoul (KR); Dong Kyung Sung, Seoul (KR)

(73) Assignee: MEDINNO INC., Gyeonggido-do (KR)

( * ) Notice: Subject to any disclaimer, the term of this patent is extended or adjusted under 35 U.S.C. 154(b) by 243 days.

(21) Appl. No.: 16/478,330

(22) PCT Filed: Oct. 31, 2017

(86) PCT No.: PCT/KR2017/012119
§ 371 (c)(1),
(2) Date: Jul. 16, 2019

(87) PCT Pub. No.: WO2018/131779
PCT Pub. Date: Jul. 19, 2018

(65) Prior Publication Data
US 2019/0374581 A1   Dec. 12, 2019

(30) Foreign Application Priority Data

Jan. 16, 2017 (KR) .................. 10-2017-0007355
Oct. 30, 2017 (KR) .................. 10-2017-0142236

(51) Int. Cl.
| | | |
|---|---|---|
| A61K 35/28 | (2015.01) | |
| A61K 35/51 | (2015.01) | |
| A61P 25/28 | (2006.01) | |
| C12N 5/0775 | (2010.01) | |
| A61K 9/00 | (2006.01) | |
| A61K 35/12 | (2015.01) | |
| A61K 35/50 | (2015.01) | |

(52) U.S. Cl.
CPC ............ *A61K 35/28* (2013.01); *A61K 9/0019* (2013.01); *A61K 9/0085* (2013.01); *A61K 35/12* (2013.01); *A61K 35/50* (2013.01); *A61K 35/51* (2013.01); *A61P 25/28* (2018.01); *C12N 5/0665* (2013.01); *C12N 2501/734* (2013.01)

(58) Field of Classification Search
CPC ...... A61K 35/28; A61K 9/0019; A61K 35/12; A61K 35/50; A61K 35/51; A61P 25/28; C12N 5/0665
See application file for complete search history.

(56) References Cited

U.S. PATENT DOCUMENTS

2015/0125950 A1* 5/2015 Lim .................... C12N 5/0668
                                                                      435/325
2016/0310534 A1  10/2016 Chang

FOREIGN PATENT DOCUMENTS

| CN | 109641013 A | 4/2019 | | |
|---|---|---|---|---|
| JP | 2017500033 A | 1/2017 | | |
| KR | 10-1661847 B1 | 9/2015 | | |
| KR | 10-2016-0078946 A | 7/2016 | | |
| KR | 10-1662405 B1 | 10/2016 | | |
| WO | WO-2015088288 A1 | * 6/2015 | .......... | A61K 9/0019 |
| WO | WO-2015164233 A1 | * 10/2015 | ............ | A61K 35/50 |
| WO | 2015-179227 A1 | 11/2015 | | |

OTHER PUBLICATIONS

Park et al. Hypothermia Augments Neuroprotective Activity of Mesenchymal Stem Cells for Neonatal Hypoxic-Ischemic Encephalopathy. Plos One 10(3): e0120893. p. 1-13 (Year: 2015).*
Ophelders et al. Mesenchymal Stromal Cell-Derived Extracellular Vesicles Protect the Fetal Brain After Hypoxia-Ischemia. STEM Cells Translational Medicine 2016; 5:754-763 (Year: 2016).*
Mitsialis et al., "Stem cell-based therapies for the newborn lung and brain: Possibilities and challenges," Semin. Perinatol., Apr. 2016, vol. 40(3), pp. 138-151.
Gonzales-Portillo et al., "Stem cell therapy for neonatal hypoxicischemic encephalopathy," Frontiers in Neurology, Aug. 12, 2014, vol. 5, No. 147, pp. 1-10.
Ophelders, Daan RMG, et al. (2016). "Mesenchymal stromal cell-derived extracellular vesicles protect the fetal brain after hypoxia-ischemia." Stem Cells Translational Medicine, 5(6), 754-763.
Hyun-Sun Lee, et al., "Priming Wharton's Jelly-Oerived Mesenchymal Stromal/Stem Cells With ROCK Inhibitor Improves Recovery in an Intracerebral Hemorrhage Model", Journal of Cellular Biochemistry, Dec. 12, 2014, 116(2): 310-319, XP055713573.
Kim, Young Seo, et al., "Hypoxia/Reoxygenation-Preconditioned Human Bone Marrow-Derived Mesenchymal Stromal Cells Rescue Ischemic Rat Cortical Neurons by Enhancing Trophic Factor Release", Molecular Neurobiology, Humana Press, US, Oct. 8, 2014, 52(1): 792-803, XP036144636.

* cited by examiner

*Primary Examiner* — Taeyoon Kim
(74) *Attorney, Agent, or Firm* — Riverside Law LLP

(57) ABSTRACT

The present invention relates to a pharmaceutical composition for preventing or treating neonatal hypoxic ischemic encephalopathy (HIE), comprising thrombin-treated stem cells or exosomes derived therefrom as an active ingredient, and a method for producing the same. According to the present invention, the thrombin-treated stem cell or the exosome derived therefrom has an increased expression of growth factors, immunoregulatory factors, antioxidation factors, or regeneration factors compared to a group not treated with thrombin and also enhances a neuronal apoptosis inhibitory effect, and thus has an advantage in that the therapeutic effect thereof on neonatal hypoxic ischemic encephalopathy (HIE) is excellent.

4 Claims, 7 Drawing Sheets

BEFORE THROMBIN TREATMENT

AFTER THROMBIN TREATMENT

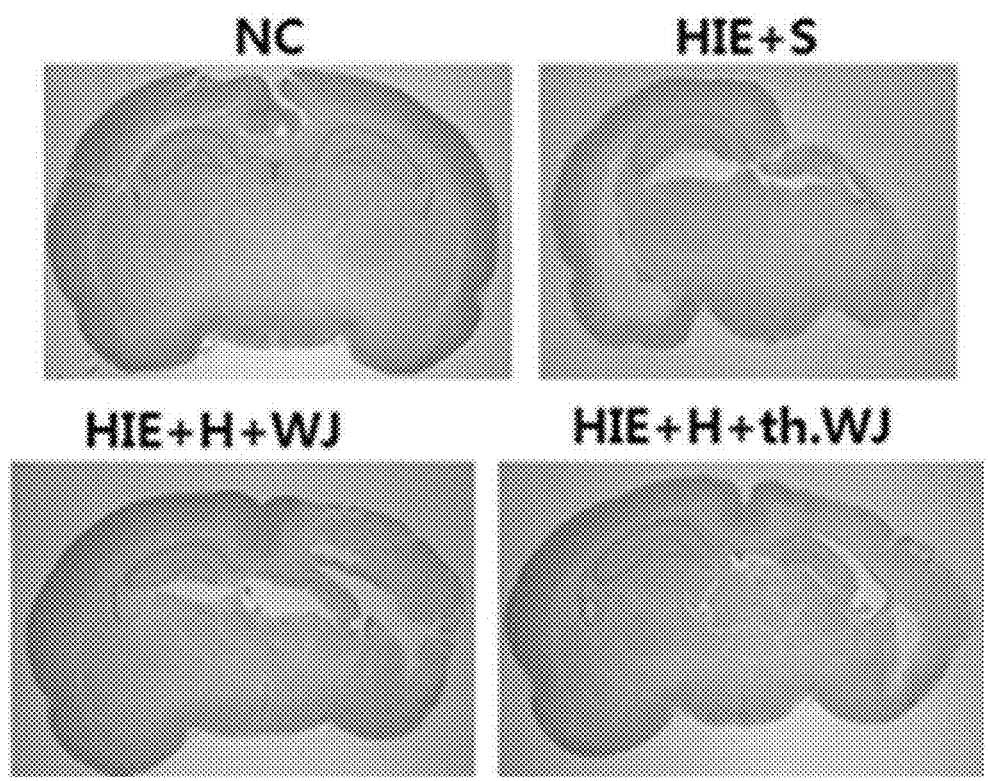

COMPOSITION FOR TREATING NEONATAL HIE

STATEMENT REGARDING GOVERNMENT RIGHTS

The present invention was undertaken with the support of Investigation for the development of new therapeutic agent with thrombin-induced, next generation, human allogeneic mesenchymal stem cells for severe neonatal hypoxic-ischemic brain injury No. HI16C1061010016 grant funded by the Korea Health Industry Development Institute (KHIDI).

CROSS-REFERENCE TO RELATED APPLICATIONS

This application is the U.S. national phase application filed under 35 U.S.C. § 371 claiming benefit to International Patent Application No. PCT/KR2017/012119, filed on Oct. 31, 2017, which is entitled to priority under to Korean Patent Application No. 10-2017-0007355, filed Jan. 16, 2017 and Korean Patent Application No. 10-2017-0142236, filed Oct. 30, 2017.

TECHNICAL FIELD

The present invention relates to a pharmaceutical composition for preventing or treating neonatal hypoxic ischemic encephalopathy (HIE), which includes thrombin-treated stem cells or an exosome derived therefrom as an active ingredient, and a method of preparing the same.

BACKGROUND ART

It has been reported that neonatal HIE accounts for 23% of the causes of all neonatal deaths, and in the case of severe damage, about 50 to 100% of patients die, and in 65 to 75% of survivors, severe motor/cognitive impairments, convulsions, etc. last throughout their lifetime. The only existing therapy for HIE is therapeutic hypothermia, but its effect is insignificant, and thus about 44% of the patients subjected to therapeutic hypothermia die or suffer from long-term neurological sequelae, and therapeutic hypothermia has no improving effect, particularly, on the severe type. For this reason, due to intractability, the development of effective and significant therapeutic methods for neonatal HIE is a very important and urgent requirement.

Moreover, since the low fertility rate in Korea is not increasing despite various government support policies, lowering the disease morbidity of the newborn will be the most efficient and reliable method for increasing the future effective economic population. Therefore, the development of next-generation high-efficacy therapeutic agents for treating neonatal HIE accounting for a significant part of overall neonatal deaths and causing serious complications during their lives is urgently needed in low fertility countries.

Meanwhile, stem cells are known as cells involved in the regeneration, treatment and immune responses of tissues as well as their differentiation potentials, and therefore there have been efforts to isolate and culture mesenchymal stem cells from the umbilical cord blood or bone marrow using these characteristics to develop them as a therapeutic agent for various diseases and symptoms. However, such a method using stem cells themselves has the following limitations and side effects.

First, basically, a cell therapeutic agent may not exclude the possibility of tumorigenicity due to DNA transfer, second, since stem cells have a large size, vascular obstruction or myocardial infarction may occur, third, there is a problem of rejection due to a cell surface antigen in transplantation (allograft) using allogeneic cells such as cord blood, and fourth, a cell therapeutic agent is generally difficult to prepare and has many limitations in storage and transportation and high production costs. As such, due to the inherent limitations of stem cells, methods of improving efficacy using gene manipulation have been developed as methods for reducing side effects and improving therapeutic effects (Korean Unexamined Patent Application No. 10-2017-0099382, etc.), but there are no clear alternatives to date.

Exosomes are membrane-structured small vesicles (with a diameter of about 30 to 100 nm) secreted from various cells, which are not directly detached from the plasma membrane, but originate from specific intracellular compartments called multivesicular bodies (MVBs) and are released and secreted out of cells, as observed in research through electron microscopy. In other words, when MVBs are fused with the plasma membrane, the vesicles are released into an extracellular environment, which are called exosomes. Although it has not been clearly known by which molecular mechanism these exosomes are produced, it has been known that various types of immune cells including B-lymphocytes, T-lymphocytes, dendritic cells, thrombocytes and macrophages as well as erythrocytes, tumor cells, and stem cells produce and secrete exosomes in a living state.

Particularly, it has been known that stem cell-derived exosomes contain nuclear components as well as receptors and proteins, and therefore are involved in intercellular communication. In addition, the stem cell-derived exosomes relatively contain less animal serum than stem cells, and thus the risk of a symptom (zoonosis) caused by animal serum infection can also be excluded. Considering the characteristics of these exosomes, cell therapy using exosomes is expected to be a new paradigm to overcome the limitations of the current stem cell therapies.

DISCLOSURE

Technical Problem

Therefore, as a result of the inventors conducting intensive studies to overcome the limitations of the existing stem cell therapeutic agents and improve therapeutic efficacy for neonatal HIE, it was confirmed that thrombin-treated stem cells/exosomes maintain the cell stability of naive stem cells, have reinforced efficacy through secretion of various growth factors and have an increased protective effect against nerve cell death, compared with naive stem cells, and thus the present invention was completed.

Accordingly, the present invention is directed to providing a pharmaceutical composition for preventing or treating neonatal HIE, which includes thrombin-treated stem cells or exosomes derived therefrom.

However, technical problems to be solved in the present invention are not limited to the above-described problems, and other problems which are not described herein will be fully understood by those of ordinary skill in the art from the following descriptions.

Technical Solution

The present invention provides a pharmaceutical composition for preventing or treating neonatal HIE, which includes thrombin-treated stem cells or exosomes derived therefrom as an active ingredient.

In one exemplary embodiment of the present invention, the stem cells are selected from the group consisting of mesenchymal stem cells, human tissue-derived mesenchymal stromal cells and human tissue-derived mesenchymal stem cells and multipotent stem cells.

In another exemplary embodiment of the present invention, the mesenchymal stem cells are derived from the umbilical cord, cord blood, bone marrow, fat, muscle, nerve, skin, amnion or placenta.

In still another exemplary embodiment of the present invention, treatment of the neonatal HIE is characterized by inhibition of nerve cell death.

In yet another exemplary embodiment of the present invention, the pharmaceutical composition is administered into a cerebral ventricle or blood vessel of a subject.

In yet another exemplary embodiment of the present invention, the pharmaceutical composition further includes a supplementary component selected from the group consisting of culture media, cytokines, growth factors and genes.

In yet another exemplary embodiment of the present invention, the thrombin-treated stem cells or exosomes derived therefrom have increased expression of growth factors, immunomodulatory factors, antioxidation factors or regeneration factors, compared with thrombin-untreated groups.

In yet another exemplary embodiment of the present invention, the growth factor is brain-derived neurotropic factor (BDNF), fibroblast growth factor (FGF), hepatocyte growth factor (HGF), nerve growth factor (NGF), or vascular endothelial growth factor (VEGF).

In addition, the present invention provides a pharmaceutical preparation for preventing or treating neonatal HIE, which contains the above composition.

In one exemplary embodiment of the present invention, the preparation is in the form for injection, infusion, or spraying.

In another exemplary embodiment of the present invention, the preparation further includes a pharmaceutically acceptable carrier.

In addition, the present invention provides a method of preparing the exosome-containing pharmaceutical composition, which includes: (a) culturing stem cells and then treating the cells with thrombin; (b) isolating exosomes from the culture solution of step (a); and (c) preparing a composition containing the exosomes isolated in step (b) as an active ingredient.

In one exemplary embodiment of the present invention, the thrombin of step (a) is included in the media at a concentration of 1 to 1000 units/mL.

In another exemplary embodiment of the present invention, the exosomes in step (c) are subjected to centrifugation.

In still another exemplary embodiment of the present invention, the centrifugation is performed at 5,000 to 500,000 g for 10 minutes to 5 hours.

In addition, the present invention provides a method for preventing or treating neonatal HIE, which includes administering thrombin-treated stem cells or exosomes derived therefrom to a subject.

In addition, the present invention provides a use of thrombin-treated stem cells or exosomes derived therefrom for preventing or treating neonatal HIE.

Advantageous Effects

According to the present invention, thrombin-treated stem cells or exosomes derived therefrom have increased expression of growth factors, immunomodulatory factors, antioxidation factors or regeneration factors and improved inhibitory effects on nerve cell death, compared with thrombin-untreated groups. Therefore, only a small amount of thrombin-treated stem cells or exosomes derived therefrom have excellent therapeutic effects on neonatal HIE. Thus, the present invention can significantly lower the production costs of the therapeutic agents.

Since the exosome-based therapeutic agent of the present invention is a cell-free preparation, there is a low risk of oncogenesis because there is no DNA, and there is no problem of transplantation rejection because there is no cell surface antigen. In addition, since the exosome-based therapeutic agent of the present invention is smaller than cells, there is no risk of blockage of microvessels in systemic administration, and since the exosome-based therapeutic agent of the present invention is a separate material, rather than cells, it can be developed as an off-the-shelf product, and thus production costs can be reduced.

Consequently, according to the present invention, the exosome-based therapeutic agent of the present invention can solve problems conventional stem cell therapeutic agents, and significantly improve therapeutic efficacy, and thus can be useful in treatment of neonatal HIE.

BRIEF DESCRIPTION OF DRAWINGS

FIGS. 6A and 6B show the results confirming the HIE therapeutic effect of thrombin-treated stem cells using an animal model.

MODES OF THE INVENTION

Figure 1:
FIG. 1 shows the results of TEM imaging analysis, confirming that exosome secretion is activated by treatment of stem cells with thrombin.
Figure 1:
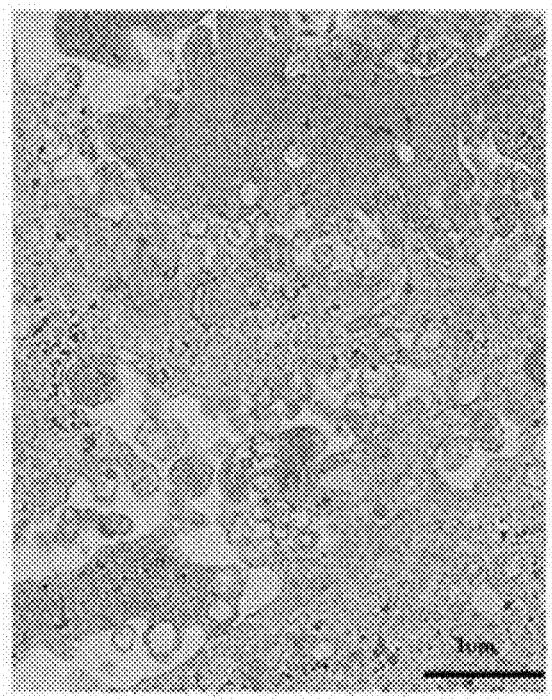

The present invention provides a pharmaceutical composition for preventing or treating neonatal HIE, which includes thrombin-treated stem cells or exosomes derived therefrom as an active ingredient.

The "stem cell" used herein refers to undifferentiated cells having self-replicability and ability to differentiate into two or more different types of cells. The stem cells of the present invention may be autologous or allogeneic stem cells, and may be derived from any kind of animal such as a human or a non-human mammal, or from an adult or an embryo, but the present invention is not limited thereto.

The stem cells of the present invention may include embryonic stem cells or adult stem cells, and preferably, adult stem cells. The adult stem cells may be mesenchymal stem cells, human tissue-derived mesenchymal stromal cells, human tissue-derived mesenchymal stem cells, or multipotent stem cells, and preferably, mesenchymal stem cells, but the present invention is not limited thereto. The mesenchymal stem cells may be derived from the umbilical cord, cord blood, bone marrow, fat, muscle, nerve, skin, amnion or placenta, but the present invention is not limited thereto.

The "cord blood" used herein means blood obtained from the umbilical vein connecting the placenta and a fetus. The cord blood, which is a byproduct naturally occurring in birth, is much easier to obtain than general mesenchymal tissue such as bone marrow that requires multiple operations. Since the cord blood storage industry has been activated and the infrastructures have already been established, it is easy to find donors. Moreover, since cord blood-derived cells are cells that do not express the histocompatibility antigen HLA-DR (class II), which is the most important cause of rejection in tissue or organ transplantation, it cannot induce or can minimize immune responses such as rejection which becomes a problem in conventional transplantation, and therefore, allogeneic cord blood as well as autologous cord blood can be used.

The "exosomes" used herein refers to membrane-structured small vesicles (with a diameter of about 30 to 100 nm) secreted from various cells, and vesicles released to extracellular environment by the fusion of MVBs and the plasma membrane. The exosomes include naturally occurring exosomes or artificially secreted exosomes.

The "hypoxic ischemic encephalopathy (HIE)" used herein refers to a condition in which brain functions or structure is changed due to severe oxygen deficiency in the brain, and although this condition may be temporary and a patient may recover therefrom, irreversible and permanent damage can occur.

The "prevention or treatment of 'HIE" used herein includes reduced, alleviated and improved symptoms of HIE, and lowering the morbidity of HIE.

The "thrombin-treated stem cells" used herein may have reinforced stem cell function/efficacy, compared with non-treated stem cells, due to increase in paracrine property, which is a main action mechanism of the stem cells, without changes in cell stability such as cell viability, oxidative function or the like. Furthermore, thrombin treatment does not only enhance the therapeutic efficacy of exosomes derived from stem cells, but also increases the secretion of exosomes.

Here, growth factors, immunomodulatory factors, antioxidation factors or regeneration factors may be increased by paracrine, and particularly, the growth factor means a protein-like physiologically active material promoting cell division, growth or differentiation, and may include BDNF, FGF, HGF, NGF, VEGF, and interleukin-6 (IL-6).

The pharmaceutical composition of the present invention may be administered to a subject via various routes without limitation, for example, orally or parenterally, and preferably administered into a cerebral ventricle or blood vessel.

The pharmaceutical composition of the present invention may further contain one or more known supplementary components having therapeutic effects for HIE. For example, the pharmaceutical composition of the present invention may further include one or more supplementary components selected from the group consisting of genes effective in HIE treatment (e.g., anti-inflammatory cytokine genes, siRNAs or anti-sense primers for inflammatory cytokines) or an expression vector including the same, cytokines providing autocrine or paracrine effects (e.g., interleukin-10), growth factors (e.g., keratinocyte growth factor), and a combination thereof.

A preferable dose of the pharmaceutical composition of the present invention may depend on a subject's condition and body weight, the severity of a disease, a drug type, an administration route and administration duration, and may be suitably selected by those of ordinary skill in the art. The composition may be administered once a day or in divided doses, but the present invention is not limited thereto.

For HIE treatment, the pharmaceutical composition of the present invention may be used independently, or in combination with surgery, radiotherapy, hormone therapy, chemotherapy, and methods using a biological reaction modulator.

The composition of the present invention may further include a suitable carrier conventionally used in preparation of a pharmaceutical composition. For example, in the case of an injection formulation, a preservative, a pain relief agent, a solubilizer or a stabilizer may be further included, and in the case of a preparation for topical administration, a base, an excipient, a lubricant or a preservative may be further included.

The composition of the present invention may be prepared by being formulated as a unit-dose preparation, suitable for administration to a subject's body according to a conventional method in the pharmaceutical field. Suitable forms for the above-mentioned purpose preferably include an injectable formulation such as an ampoule for injection, an infusion formulation contained in an infusion bag, and a spray formulation such as an aerosol as a preparation for parenteral administration. The ampoule for injection may be prepared by being mixed with an injection solution immediately before use, and as an injection solution, physiological saline, glucose, or a Ringer's solution may be used. In addition, the infusion bag may be made of polyvinyl chloride or polyethylene. In the present invention, administration means providing a predetermined composition of the present invention to a subject by any suitable method.

A preferable dosage of the pharmaceutical composition of the present invention varies according to the condition and body weight of a subject, the severity of a disease, drug type, administration route or the duration of administration, and may be suitably selected by those of ordinary skill in the art. The administration of the composition may be performed once a day or in divided doses, but the present invention is not limited thereto.

In addition, the present invention provides a method of preparing the exosome-containing pharmaceutical composition, which includes: (a) culturing stem cells and then treating the cells with thrombin; (b) isolating exosomes from the culture solution of step (a); and (c) preparing a composition containing the exosomes isolated in step (b) as an active ingredient.

In the present invention, the concentration of thrombin treatment may be sufficient where it enhances the efficacy of stem cells/exosomes. Although the concentration is not particularly limited, it is preferably 1 to 1000 units/mL in a media.

In the present invention, there is no limitation to a method of isolating exosomes, and exosomes may be isolated from a culture solution by centrifugation, ultracentrifugation, filtration through a filter, gel filtration chromatography, free-flow electrophoresis, capillary electrophoresis, isolation using a polymer or a combination thereof, and preferably, centrifugation/ultracentrifugation. Here, the centrifugation/ultracentrifugation may be performed at 4° C. and 5,000 to 500,000 g for 10 minutes to 5 hours.

The "media used in cell culture" used herein means a mixture for in vitro growth and proliferation of cells, for example, stem cells. The mixture includes essential factors for cell growth and proliferation, such as glucose, amino acids, various types of nutrients, serum, growth factors, and minerals. Media that can be used in the present invention may include commercially produced or artificially synthesized media such as Dulbecco's Modified Eagle's Medium (DMEM), Minimal Essential Medium (MEM), Basal Medium Eagle (BME), RPMI1640, Dulbecco's Modified Eagle's Medium: Nutrient Mixture F-10 (DMEM/F-10), Dulbecco's Modified Eagle's Medium: Nutrient Mixture F-12 (DMEM/F-12), a-Minimal essential Medium (α-MEM), Glasgow's Minimal Essential Medium (G-MEM), Isocove's Modified Dulbecco's Medium (IMDM) and KnockOut DMEM, but the present invention is not limited thereto.

Hereinafter, to help in understanding the present invention, exemplary examples will be suggested. However, the following examples are merely provided to understand the present invention, more easily and not to limit the present invention.

EXAMPLES

Example 1: Induction of Enhanced Efficacy by Treatment of Stem Cells with Thrombin 1-1. Induction of Exosome Secretion by Thrombin Human cord blood-derived mesenchymal stem cells ($3\times10^5$) were seeded on a 60-mm culture dish (Orange Scientific cat #4450200), and cultured for 1 week. After confirming that the cells were saturation-proliferated in the culture dish, the culture media was replaced with a serum-free culture medium (MEM alpha medium) in which 50 units/mL thrombin (REYON Pharmaceutical. Co., LTD) was diluted, and the cells were incubated again for 6 hours, thereby obtaining thrombin-treated stem cells.

Afterward, to confirm whether exosome secretion in mesenchymal stem cells was activated by thrombin treatment, a process of the exosome secretion was confirmed by transmission electron microscopy (TEM) images. As a result, as shown in FIG. 1, it can be seen that thrombin stimulation induces exosome secretion.

The culture solution was dispensed into centrifuge tubes and subjected to centrifugation at 4° C. and 100,000 rpm for 30 minutes, and supernatant was transferred to a new tube so as to remove cell debris. Again, the supernatant was ultra-centrifuged at 4° C. and 100,000 rpm for 2 hours, and then supernatant was removed again, thereby obtaining exosomes (final concentration: 15 μg/mL).

Figure 2:
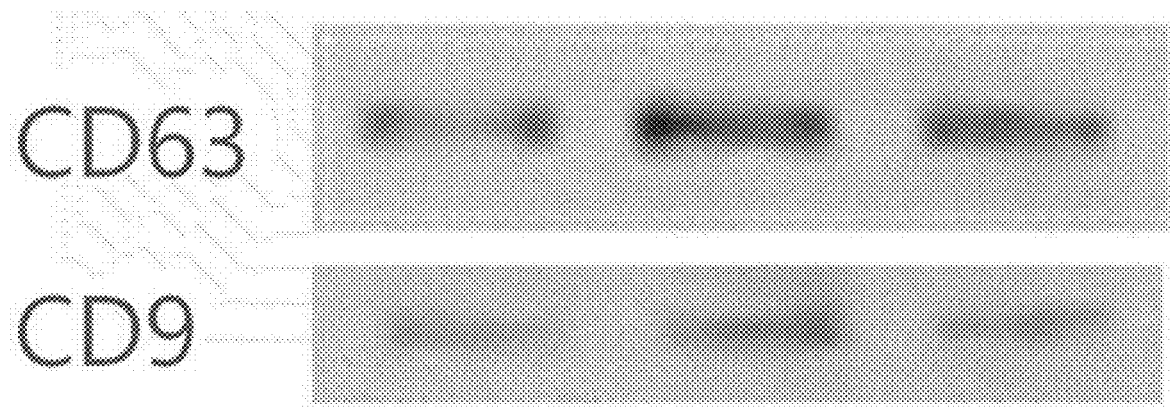
FIG. 2 shows the western blotting result, confirming whether CD63 and CD9, which are exosome markers, are normally expressed in thrombin-treated stem cell-derived exosomes.

Here, to confirm whether the obtained product includes exosome, the expression of known exosome markers such as CD63 and CD9 (System Biosciences, Mountain View, CA, USA) was verified through western blotting. As a result, as shown in FIG. 2, products obtained from thrombin-treated stem cells express CD63 and CD9, confirming they include exosomes.

1-2. Enhanced Stem Cell/Exosome Efficacy by Thrombin

It was confirmed whether the stem cells and exosomes obtained in Example 1-1 had increased expression of growth factors or anti-inflammatory cytokines by thrombin treatment.

Specifically, cell membranes were lysed using a lysis buffer to isolate proteins from the cells/exosomes, and BDNF, FGF, HGF, NGF, VEGF and IL-6 levels were measured using a Procarta immunoassay kit (Affymetrix, USA).

Figure 3:
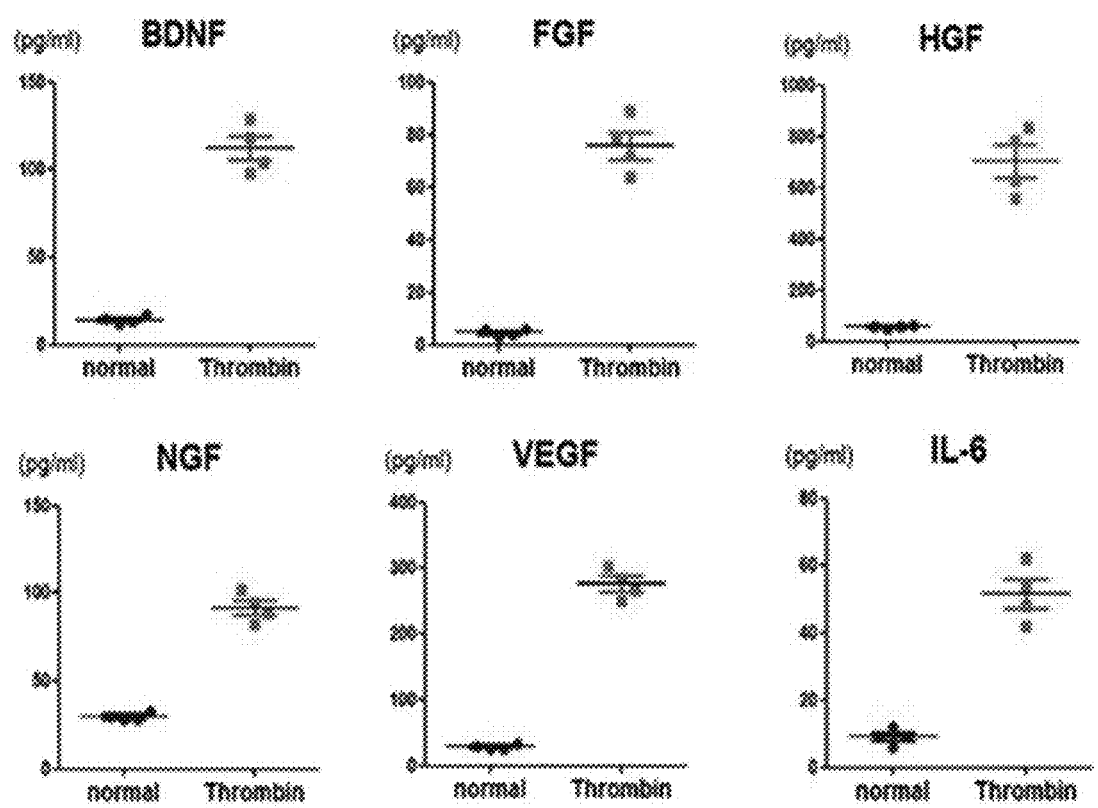
FIG. 3 shows the immunoassay results, confirming that the expression of growth factors (BDNF, FGF, HGF, NGF and VEGF) and an anti-inflammatory cytokine (IL-6) in stem cells and exosomes are increased due to thrombin treatment.

As a result, as shown in FIG. 3, the expression of BDNF, FGF, HGF, NGF, VEGF and IL-6 was increased by thrombin treatment, compared with that in thrombin-untreated stem cells or exosomes obtained therefrom (control; normal).

This result shows that cell regeneration, blood vessel regeneration, and anti-inflammatory efficacy of stem cells or exosomes derived therefrom are enhanced due to thrombin treatment.

Example 2: Extablishment of In Vitro Model of Neonatal HIE

After 18.5 days of pregnancy, the lower abdomen of a SD rat was dissected to take out a fetus, and then the whole brain was carefully extracted. Only the cerebral cortex was carefully separated from the extracted brain tissue, separated into single cells using a pipette, and then cultured in a nerve cell culture solution. After 10 days of culture, the cells were exposed to a glucose-free medium under a 1% hypoxic condition (oxygen and glucose deprivation (OGD)) for 60 minutes, thereby constructing an in vitro model of neonatal HIE.

Example 3: In Vitro Inhibitory Effect of Thrombin-Treated Stem Cells on Nerve Cell Death The in vitro neonatal HIE model established in Example 2 was treated with the thrombin-treated stem cells obtained in Example 1, and then nerve cell viability was assessed by MTT assay.

Figure 4:
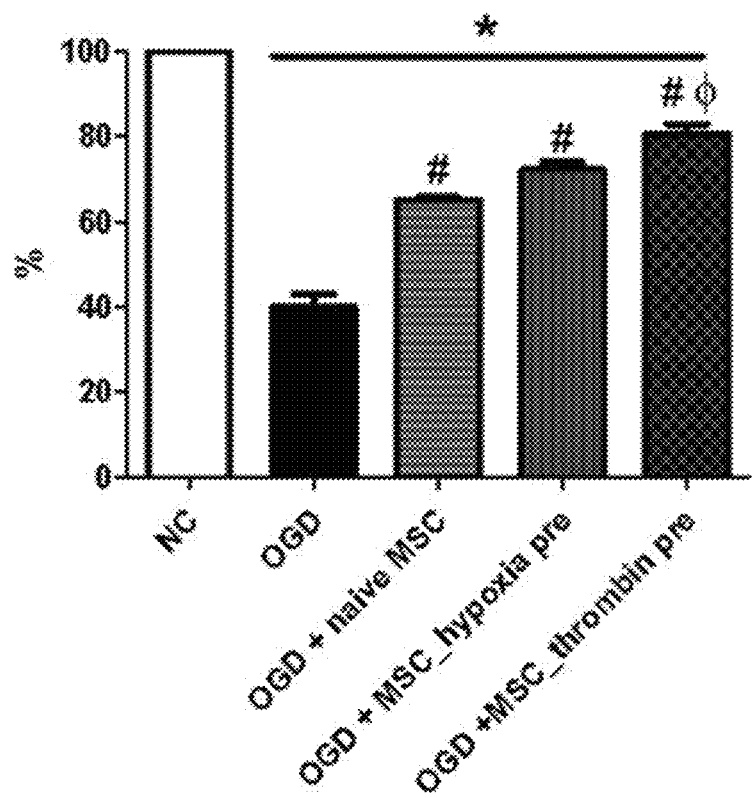
FIG. 4 shows the MTT assay result showing the inhibitory effect of thrombin-treated stem cells on nerve cell death in an in vitro HIE model.

As a result, as shown in FIG. 4, compared with normal nerve cells (NC), in the in vitro HIE model (OGD), nerve cell death was significantly increased due to oxygen/glucose deprivation, whereas, in the "thrombin-pretreated stem cell-treated in vitro neonatal HIE group (OGD+MSC thrombin pre)," compared with the thrombin-untreated stem cell group (OGD+naive MSC) or the hypoxia-pretreated stem cell group (OGD+MSC hypoxia pre), nerve cell death was considerably inhibited, demonstrating that the thrombin-treated stem cells exhibited the most excellent nerve cell protective effect.

Example 4: In Vitro Inhibitory Effect of Thrombin-Treated Stem Cell-Derived Exosomes on Nerve Cell Death The in vitro neonatal HIE model established in Example 2 was treated with the thrombin-treated stem cell-derived exosomes obtained in Example 1, and nerve cell viability was assessed by MTT assay.

Figure 5:
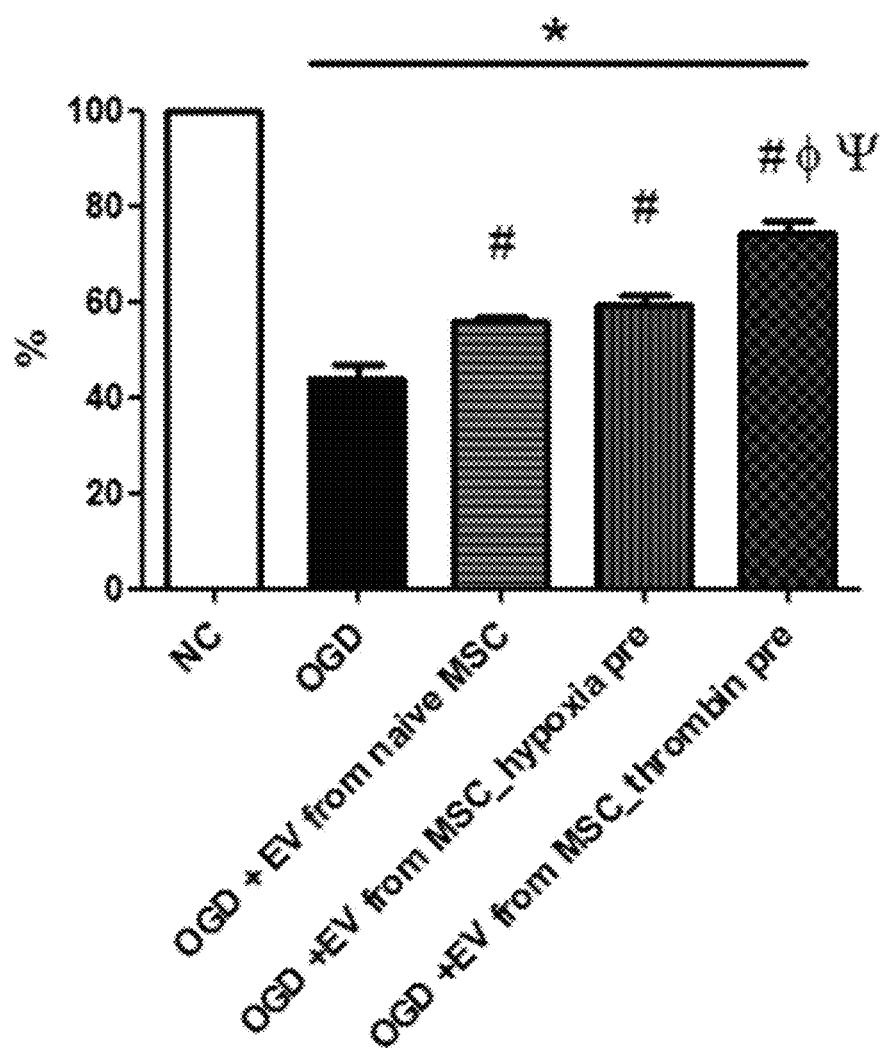
FIG. 5 shows the MTT assay result showing the inhibitory effect of thrombin-treated stem cell-derived exosomes on nerve cell death in an in vitro HIE model.

As a result, as shown in FIG. 5, compared with normal nerve cells (NC), in the in vitro HIE model (OGD), nerve cell death was significantly increased due to oxygen/glucose deprivation, whereas, in the "thrombin-pretreated stem cell-derived exosome-treated neonatal HIE group (OGD+EV from MSC thrombin pre)," compared with the thrombin-untreated stem cell-derived exosome-treated group (OGD+ EV from naive MSC) or the hypoxia-pretreated stem cell-derived exosome-treated group (OGD+EV from MSC hypoxia pre), it was confirmed that nerve cell death was significantly inhibited.

Therefore, like the thrombin-treated stem cells of the present invention, it was also verified that the exosomes derived therefrom exhibited an excellent nerve cell protective effect.

Example 5: Verification of Therapeutic Activity of Thrombin-Treated Stem Cells on HIE (In Vivo)

To confirm the therapeutic activity of thrombin-treated stem cells on HIE using animal models, an experiment was performed as follows.

Figure 6B:
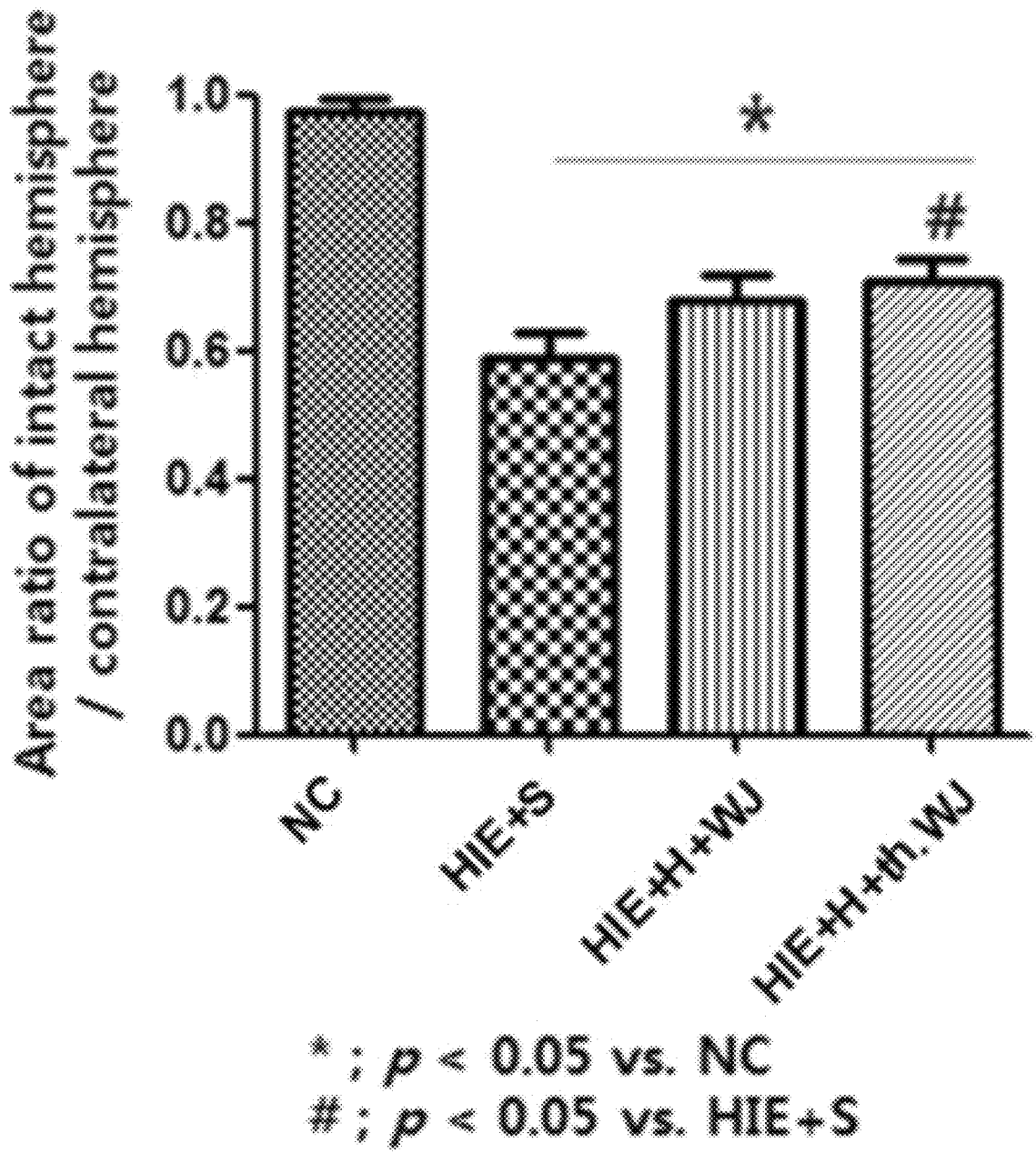

Today, therapeutic hypothermia is the only palliative therapy clinically applied for treating HIE. For this reason, also in the animal experiment, similar to a clinical environment, after HIE was induced, the animal model was subjected to therapeutic hypothermia. It was examined whether the disease was improved while stem cells were further added for combined treatment. Groups classified for the experiment are as follows:

(1) NC: normal control
(2) HIE+S: diseased control (after the induction of the disease, treated with saline)
(3) HIE+H+WJ: treated with thrombin-untreated stem cells after hypothermia treatment was applied
(4) HIE+H+Th.WJ: treated with thrombin-treated stem cells after hypothermia treatment was applied As a result, as shown in FIGS. 6A and 6B, compared with the NC group, it was confirmed that, in all of the disease-induced HIE groups, area of brain injury was significantly increased. In the HIE+H+WJ group, the injured area tended to be improved, but there was no significance. However, in the HIE+H+Th.WJ group, the injured area was further improved, and statistically significance.

It should be understood by those of ordinary skill in the art that the above description of the present invention is exemplary, and the exemplary embodiments disclosed herein can be easily modified into other specific forms without departing from the technical spirit or essential features of the present invention. Therefore, the exemplary embodiments described above should be interpreted as illustrative and not limited in any aspect.

INDUSTRIAL APPLICABILITY

According to the thrombin-treated stem cells or exosomes derived therefrom according to the present invention, even with a small amount, a treatment effect against neonatal HIE is excellent. Problems of conventional stem cell therapeutic agents can be solved, and their therapeutic efficacy can be significantly improved by thrombin treatment. Therefore, the thrombin-treated stem cells or exosomes derived therefrom according to the present invention can be useful in treatment of neonatal HIE.

The invention claimed is:

1. A method of treating a subject suffering from neonatal hypoxic ischemic encephalopathy (HIE), comprising;
   treating mesenchymal stem cells derived from umbilical cord or umbilical cord blood with 50 units/mL of thrombin for 6 hours, and
   administering the thrombin-treated mesenchymal stem cells into the subject,
   wherein the subject suffering from HIE is treated by therapeutic hypothermia prior to the administering the thrombin-treated mesenchymal stem cells, and wherein said thrombin-treated mesenchymal stem cells are administered into a cerebral ventricle or blood vessel.

2. The method of claim 1, wherein the thrombin-treated stem cells further comprises a supplementary component selected from the group consisting of culture media, cytokines, growth factors and genes.

3. The method of claim 1, wherein the thrombin-treated mesenchymal stem cells are in the form for injection, infusion, or spraying.

4. The method of claim 1, wherein the thrombin-treated mesenchymal stem cells further comprise a pharmaceutically acceptable carrier.

* * * * *